United States Patent [19]

Hainrihar et al.

[11] Patent Number: 5,525,597

[45] Date of Patent: Jun. 11, 1996

[54] SYNERGISTIC INSECTICIDAL COMPOSITIONS COMPRISING CAPSICUM AND INSECTICIDAL USE THEREOF

[75] Inventors: Gary C. Hainrihar, Lawton, Mich.; James G. Dubberly; John T. Greenlee, both of Greenville, Miss.

[73] Assignee: Kalamazoo Holdings, Inc., Kalamazoo, Mich.

[21] Appl. No.: 166,695

[22] Filed: Dec. 14, 1993

[51] Int. Cl.$^6$ ..................................... A01N 57/00

[52] U.S. Cl. .......................... 514/75; 514/128; 514/132; 514/627; 514/724; 424/195.1; 424/DIG. 10

[58] Field of Search ............... 424/195.1, DIG. 10; 514/724, 75, 132, 128, 627

[56] References Cited

U.S. PATENT DOCUMENTS

| | | | |
|---|---|---|---|
| 312,270 | 2/1885 | Hoag | 424/195.1 |
| 436,848 | 9/1890 | Farwell | 424/195.1 |
| 930,549 | 8/1909 | Lechner | 424/697 |
| 2,159,953 | 5/1939 | Proetto | 424/195.1 |
| 4,820,517 | 4/1989 | Pfeiffer | 424/195.1 |
| 5,227,162 | 7/1993 | Ferrari | 424/195.1 |

*Primary Examiner*—John W. Rollins
*Attorney, Agent, or Firm*—Gordon W. Hueschen

[57] ABSTRACT

Insecticidal compositions, comprising normally-employed insecticides but comprising also an effective activity-enhancing amount of capsaicin or other capsaicinoid, especially in the form of capsicum, exhibit synergistic effects against numerous insects, including especially bud worms, boll worms, cabbage loopers, army worms, beet army worms, and beetles, and are especially effective on cotton, soybeans, common garden vegetables, and flowers, when sprayed on the insect or its habitat, especially as an aqueous solution, suspension, or emulsion. Larger crop stands may be effectively treated by aerial spraying from the usual crop-dusting airplane.

42 Claims, No Drawings

SYNERGISTIC INSECTICIDAL COMPOSITIONS COMPRISING CAPSICUM AND INSECTICIDAL USE THEREOF

BACKGROUND OF THE INVENTION

1. Field of the Invention

Insecticidal compositions comprising normally-employed insecticidally-active agents but comprising an activity-enhancing amount of capsaicin or other capsaicinoid, especially in the form of capsicum, and the insecticidal employment thereof. According to the present invention, it has been found that the employment with normally-employed insecticidally-active agents of activity-enhancing amounts of capsaicin or other capsaicinoid, especially in the form of capsicum, but also including synthetic capsaicinoids such as the vanillyl amide of pelargonic acid, produces synergistic effectiveness in combatting numerous insects, especially boll worms, beet army worms, loopers, beetles, and bud worms, in actual field applications. As used herein, the term "capsaicinoid" is broad enough to encompass capsaicin and amounts thereof contained in capsicum.

2. Prior Art

The prior art is replete with innumerable insecticidally-active agents and compositions thereof. Nevertheless, existing insecticidal agents and compositions continue to exhibit less than optimum effectiveness, especially when employed in an attempt to control certain insects, and specially upon certain living plants and crops.

Known prior art discloses the employment of capsaicinoids as insect as well as animal and human repellents. They have also been used as optional ingredients of miticides in combination with elemental sulphur plus garlic extract, as a pesticide for snails, as an ingredient of a paint on the interior of beehives or on the exterior of boats, and they have also been used as a component of aerosols for crowd control and in personal protective devices.

The following Examples show that capsaicinoids are not toxic to insects, when used alone, and the observations of the inventors in this regard is similar to the known effect of capsaicinoids on humans. For example, hot peppers of the Capsicum genus have been used as condiments in foods for centuries, and extracts thereof are classified as "GRAS" by the US Food and Drug Administration. They moreover have EPA approval for use in self-defense and crowd-control aerosols.

The prior art in this field has been searched. In two (2) separate searches conducted in United States Class 424 subclass 195.1, Class 514 subclass 627, and in the APS full-text data base, as well as in US Class 424, subclasses 45, 48, 195.1, and 405 and US Class 514 subclasses 918 and 919, the essence of the present invention was not found to be disclosed or suggested.

The most relevant US patents turned up in the searches were as follows:

U.S. Pat. No. 312,270 Hoag, issued Feb. 17, 1985:

Hoag provides a mixture of capsicum, Helloboro, Paris Green, sugar, and carbolic acid and uses this mixture as an insecticide. Paris green (copper acetoarsenite) and carbolic acid are strong poisons which would kill anything in sight, even if it was an insect, whereas it would appear that the capsicum was employed as a repellant because of its noxious properties, although such is not stated. In the presence of Paris green and carbolic acid, any insecticidal effect of capsicum would surely have been masked, if existent.

U.S. Pat. No. 436,848 Farwell, issued Sep. 23, 1890:

Farwell provides insecticides for external application to animals to avoid annoyances by insects, which preparation must not irritate the skin and which must yet retain the essentials for driving away the insects. It consists of "water-pepper", *Polygonum hydropiper*, which is unrelated to the Capsicum genus. It further belongs to the order Polygonaceae, whereas Capsicum belongs to the order Solanaceae. The formulation of Farwell also contains wormwood, a member of the Artemisia family, which is known to be high in essential oils containing thujone. This patent in no way suggests the use of capsaicin or capsicum for its intended purpose according to the present invention.

U.S. Pat. No. 930,549 Lechner, issued Aug. 10, 1909:

Lechner claimed an insecticide comprising benzene as a solvent, poke-root, alum, and red pepper, but does not describe the purpose of the red pepper. Lechner considers the smell of the poke-root as the permanent repellent, but fails to describe the role played by the capsicum, which is not identified as an insecticide.

U.S. Pat. No. 2,159,953 Proetto, issued May 23, 1939:

Proetto prepares a combination of wine dregs, capsicum, African bitter gourd juice, nicotine, and strong alkalized soap solution for use an as insecticide. He states at Column 2, lines 46–50, that the combination of capsicum, the African bitter gourd juice, and the wine dregs constitutes a death-dealing combination of ingredients, whereas the nicotine is present as a narcotic. He goes on to state at page 2, Column 1, lines 1–4, that the nicotine and alkalized soap may be omitted in some instance, although all the claims of this patent include both of these ingredients. According to Merck Index, 11th Edition, page 6431, nicotine is a powerful commercial insecticide identified, inter alia, as "Black Leaf 40™", described as being highly toxic and useful in a soap as a contact poison. The combination of capsicum, African bitter gourd juice, and wine dregs in the presence of the nicotine and soap certainly leaves the role of the individual ingredients undefined, especially since the nicotine in the presence of soap is a highly toxic ingredient. The capsicum most probably serves only as a repellant. It is not employed in oleoresin form.

U.S. Pat. No. 4,820,517 Pfeiffer, issued Apr. 11, 1989:

Pfeiffer prepares a fraction of black pepper extract which is insecticidal. This fraction is non-irritating as pointed out in his Column 1, lines 51–60, which is not a characteristic of capsaicin, which is very irritating to human beings. The active principle of Pfeiffer is of unknown composition, but black pepper *Piper nigrum*, is unrelated to Capsicums, and the principle in black pepper which causes "bite" is piperine, a compound which is chemically distinct from capsaicin and other capsaicinoids. Pfeiffer accordingly does not show or suggest either the compositions or the method of the present invention.

U.S. Pat. No. 5,227,162 Ferrari, issued Jul. 13, 1993:

Ferrari shows an acaracide comprising ethanol, garlic pulp, elemental sulphur, and optionally capsicum (Column 1, lines 53–68). Capsicum is present in his preferred mixture and in some of his claims. The exact role of each of the ingredients is left in doubt but, in any event, since arachnids are not insects, Ferrari can provide no showing or suggestion or either the composition or method of the present invention.

As seen from the foregoing, the searches failed to reveal previous patent literature considered to be even close to the present development and a search of the APS full-text data base was also unproductive.

A problem constantly facing farmers with the need to control insects attacking plants and crops is the slow loss of activity which insecticides develop as resistance thereto builds up. There is always a need for improved materials which are not only more effective against particular insects, but which are also versatile and can be used to combat a wide spectrum of insects. Such improvements are seldom achieved by the use of a single insecticide. Nevertheless, whether mixtures of insecticides or single individual insecticides are employed, it is always of great value to find some manner in which their insecticidal activity can be enhanced.

It has now been found that mixtures of insecticides with capsaicin or other capsaicinoid, or capsicum containing the same, have valuable and unexpected properties in that the insecticidal activity of the admixture is greater than would be expected and synergism is exhibited of a kind which is especially effective in the context of certain crops such as cotton, soybeans, and the like.

Accordingly, the present invention provides an insecticidal composition comprising an admixture of an active insecticide and an activity-enhancing amount of a compound selected from capsaicin, other capsaicinoids, and capsicum containing the same.

OBJECTS OF THE INVENTION

It is an object of the present invention to provide new and improved insecticidal compositions having enhanced activity due to the presence of an activity-enhancing amount of capsaicin or other capsaicinoid, especially in the form of capsicum, in an insecticidal composition containing an active ingredient which is normally effective as an insecticide.

Another object of the invention is to provide a method of employing such activity-enhanced compositions for the elimination of insects which are damaging either as such or in the form of their larvae to growing plants and crops, such as cotton, soybeans, common garden vegetables and flowers, and the like. A further object is the provision of such insecticidal compositions which have enhanced effectiveness against boll worms, beet army worms, loopers, Japanese and other beetles, and bud worms. Still a further object of the invention is the provision of such compositions and method which are effective in use in actual field applications, and particularly when applied to the insect or its habitat in the form of an aqueous solution, suspension, or emulsion as a spray, including an aerosol spray, and suitable for application to large stands of crops in the form of an aerial spray by a crop-dusting type airplane.

Yet another object of the invention is the provision of such compositions and method wherein the capsaicin is provided in the form of capsicum, which in turn is preferably provided in the form of Capsyn™, as hereinafter identified.

Still other objects will become apparent hereinafter and yet additional objects will be obvious to one skilled in the art to which this invention appertains.

SUMMARY OF THE INVENTION

The present invention, then, comprises the following aspects, inter alia, singly or in combination:

An insecticidal composition comprising as essential ingredients an effective insecticidal amount of (A) an insecticidal ingredient, plus (B) an activity-enhancing amount of a capsaicinoid; such a composition for insect control comprising the insecticidal-activity-enhanced composition in a weight ratio of (B) to (A) of between about 1:10 and 1:500; such a composition wherein the weight ratio of (B) to (A) is between about 1:10 and 1:200–400; such a composition wherein the weight ratio of (B) to (A) is approximately 1:100 to 1:400; such an effective insecticidal composition having enhanced insecticidal activity comprising an insecticidally-effective amount of an insecticidal ingredient or ingredients, and an activity-enhancing amount of capsaicin; such an insecticidal composition comprising a mixture of (A) an insecticidal ingredient or ingredients, and (B) an activity-enhancing amount of capsaicin in a ratio between about 1:10 to 1:500 by weight, the concentration of the insecticidal ingredient or ingredients being an insecticidally-effective concentration; such a composition in the form of a dilutable concentrate; such a composition wherein the composition is dilutable with water.

Also, a method of killing insects comprising the step of spraying a combination of (A) an effective insecticidal amount of an insecticidal ingredient, plus (B) an acitivity-enhancing amount of a capsaicinoid, upon the insect or upon its habitat; such a method for controlling insects comprising contacting insects or their habitat with an insecticidally-active composition; such a method of controlling insects which comprises applying, to the insects or their habitat, an insecticidally-effective amount of such a composition; such a method wherein the concentration of active ingredients in the composition is between about 0.001 and 20% by weight; such a method wherein the concentration of active ingredients in the composition is between about 0.005 and 10% by weight; such a method wherein the habitat is living plants; such a method wherein the plants are cotton, soybeans, corn, garden vegetables, fruits, or flowers; such a method wherein the plants are cotton plants; such a method wherein the weight ratio is between about 1:100 and 1:400 by weight; such a method wherein the composition is applied by spraying; such a method wherein the composition is applied by aerial spraying; such a method in which active ingredients are applied at a rate of about 0.8 to about 5.5 pounds per acre; such a method wherein the composition is applied at a rate of about 2.2 to about 5.36 pounds per acre; such a method wherein the composition is applied at a rate of about 0.45 to about 2.25 pounds per acre; such a method wherein the insect controlled is selected from boll worms, army worms, bud worms, loopers, and beetles.

Moreover, a method of enhancing the insecticidal activity of an insecticide composition comprising the step of including in said composition an effective insecticidal-activity-enhancing amount of a capsaicinoid; such a method wherein the weight ratio of capsaicinoid to insecticide is between about 0.1 and about 20% by weight; such a method wherein the weight ratio of capsaicinoid to insecticide is between about 0.2 and about 10% by weight; such a method wherein the insecticidal activity enhancer is capsaicin; such a method wherein the insecticidal activity enhancer is oleoresin capsicum; such a composition wherein the insecticidal activity enhancer is capsaicin; such a method wherein the insecticide is selected from the group consisting of chlorpyrifos, phosphorothioates, thiodicarb, parathions, methomyl, profenfos, and pyrethrins; such a composition wherein the insecticide is selected from the group consisting of chlorpyrifos, phosphorothioates, thiodicarb, parathions, methomyl, profenfos, and pyrethrins; such a method wherein the insect controlled is selected from the group consisting of bud worms, boll worms, cabbage loopers, army worms, and beetles, and the habitat protected is a plant selected from the group consisting of cotton, beans, corn, garden vegetables, fruits, and flowers; such a method wherein the enhancement relates to the protection of a plant selected from the group consisting of cotton, beans, corn, garden vegetables, fruits, and flowers against an insect selected from the group consisting of bud worms, boll worms, cabbage loopers, army worms, and beetles; and such a method wherein the enhancement is of an insecticide selected from the group consisting of chlorpyrifos, phosphorothioates, thiodicarb, parathions, methomyl, profenfos, and pyrethrins.

Finally, such a composition or method wherein the capsicum, capsaicinoid, or capsaicin is in the form of an essentially lipid-free and optionally aqueous solution in a polyol such as ethylene glycol, propylene glycol, glycerine, or the like.

Glossary of Terms:

Insecticides which may be employed include the following, were manufactured by the companies identified hereinafter, and contained the following active ingredients:

Lorsban—A trademarked product of Dow Chemical Co., containing Chlorpyrifos.

Karate—A trademarked product of the ICI Argrochemicals, Inc., containing synthetic pyrethroids.

Larvin—A trademarked product of Union Carbide, containing ethanimidothioic acid. (Thiodicarb.)

Curacron—A trademarked product of Ciba-Geigy, containing Profenfos, O-(4-bromo-2-chlorophenyl)-O-ethyl-S-propyl phosphorothioate.

Thiodicarb—Active ingredient of Larvin. Merck Index XI number 9258 on page 1469.

Chlorpyrifos—Active ingredient of Lorsban. Merck Index XI number 2190 on page 339.

Methomyl—Active ingredient of Lannate, Nudrin, and Insecticide 1179, Merck Index XI, number 5905 on page 944. DuPont's Lannate active ingredient.

Pyrethrum Flowers—Natural plant constituent containing pyrethrin, having insecticidal activity, from Chrysanthemum cineriaefolium. Merck Index XI, number 7980 on page 1267.

Pyrethrins—Active insecticidal constituents of Pyrethrum Flowers, Merck Index XI, number 7978, page 1266. Term includes synthetic pyrethroids.

Ortho Rose and Flower Insect Killer—comprising as active ingredients 0.02% pyrethrins, 0.20% piperonal butoxide as an adjuvant-synergist. Product of Chevron Chemical Co.

Parathion—Insecticide. Merck Index XI, number 6983, page 1113.

Methyl Parthion—a standard 21% solution. PennCap M® insecticide, Elf Atochem North America, E.P.A. Reg. No. 4581-292. Non-systemic contact and stomach insecticide. Merck Index XI, number 6022, page 959.

Methyl Demeton—Parathion type insecticide. Merck Index XI, number 5971, page 952.

Ovasyn—Amitraz (CAS 33089-61-1).

Some additional insecticides which may be employed are listed by the American Association of Economic Entomologists in its latest compendium and, representatively, those listed in its Jan. 10, 1952 compilation, as reported on pages 748–750 under the heading "Insecticides" in The Yearbook of Agriculture for 1952 entitled "Insects" by the USDA and printed and sold by the Superintendent of Documents, Washington 25, D.C.

The following is the preferred form of capsaicin, capsaicinoids, or capsicum, which makes it more conveniently dispersible/soluble in water.

Capsyn™—A solution of oleoresin capsicum in propylene glycol, essentially free of lipids and fats, carotenoids, and capsicum triglycerides (i.e., defatted oleoresin capsicum in propylene glycol), and containing about 2% capsaicinoids obtained from cayenne pepper pods, a product of Kalsec, Inc., Kalamazoo, Mich.

An essentially lipid-free and optionally aqueous solution of the capsicum, capsaicinoid, or capsaicin in a polyol such as ethylene glycol, propylene glycol, glycerine, or the like, but preferably in propylene glycol, is therefore the preferred form for ready dispersibility and employment according to the methods and composition of the invention.

The Activity-Enhancing Ingredient

The insecticidal activity-enhancing ingredient according to the present invention is capsaicin, identified in the Merck Index, 11th Edition, as number 1767, "Capsaicin", the trans-8-methyl-N-vanillyl-6-nonenamide. It is contained in capsicum, number 1769 of the same Merck Index, in a percentage of between 0.1 and 1% by weight. Other capsaicinoids, including synthetic capsaicinoids, such as the vanillyl amide of pelargonic acid, may also be employed, inasmuch as these have the same irritating and noxious properties as natural capsaicinoids and especially capsaicin. The stereoisomer, the cis compound, may also be employed but is not preferred inasmuch as it is less irritating than the trans isomer.

THE INVENTION

According to the present invention, the activity-enhancing and synergistic effect of the capsaicinoids is demonstrated by the following Examples, which also show that the capsaicinoids are not insecticides by themselves.

According to the present invention, the capsaicin or other capsaicinoids are suitable for direct admixture and application together with or in admixture with commercial insecticides at their EPA-labelled rates and formulations and for application of the combination to the insect or its habitat as by spraying, dusting, or the like. Although the admixtures may be employed in powder form, aqueous solutions and dispersions or suspensions are preferred. The resulting capsaicin-containing sprays are extremely noxious and incite coughing in human beings, thereby making the combinations safer for use than when the capsaicin or other capsaicinoid, e.g., capsicum, is not present. This safety factor results because protective breathing apparatus can not be forgotten when using the compositions of the present invention, whereas there is often a tendency to neglect protection when normal commercial insecticides are employed alone. However, it is clear and should be obvious that a downwind draft will be noticed immediately when a combination of normal commercial insecticide and capsicum is employed according to the present invention.

The preferred form of capsaicin and capsicum is Capsyn™, which is a solution of the capsaicinoid oleoresin capsicum derived from Capsicum sp. in propylene glycol, essentially free of triglycerides, fats, and carotenoids. It is water dispersible and the combination of the Capsyn™ and the insecticide according to the present invention remains in aqueous solution or suspension as a cloudy admixture. It does not leave a residual color on plant material, such as cotton. In less preferred forms, this may be the case. For instance, in a less preferred form of an oil solution of the capsicum extract, optionally but preferably emulsified with an emulsifier such as Polysorbate 80™, the oil solution may sometimes somewhat interfere with the effect of emulsifiers employed for dispersion or emulsification of the insecticidal composition and, moreover, may sometimes stain the foliage as well as develop rancid aromas which, of course, is the exact reason why such oil solutions are not preferred.

The combinations or admixtures of the invention are active against a wide range of insects, and one of their advantages stems from the fact that they can be applied to a crop attacked by insects at any stage of their life cycle as long as the basic insecticide is similarly flexible. This is an important advantage since the timing of insecticide application thus becomes less critical and there is a greater chance of obtaining good overall control in a single treatment. In addition to their synergistic activity, an extension of the spectrum of control of resistant insects is observed.

The compositions and method of the present invention exhibit an enhanced insecticidal effectiveness generally against all types of insects, especially of the class Insecta.

Included in the list of insects against which the enhanced insecticidal activity is provided according to the present invention are the following: beetles, especially of the order Coleoptera; as well as boll weevils identified as *Anthonomus grandis*, boll worms and corn earworms and moth larvae associated therewith. Any of numerous army worms and larvae of moth which destroy grass, grain, and other crops, especially the common army worm *Pseudoletia unipuncta*. Weevils of all sorts, especially of the group Rhynchophora which as minute beetles are especially injurious as larvae to grain, to living plants, and to cotton and the like.

Among the insects which the present mixtures are able to control are insects such as aphids, for example the green peach aphid *Myzus persicae;* the boll weevil *Anthonomus grandis*; and noctuid insects such as for example the bollworm *Hellothis zea*, pink bollworm *Pectinophora gossypiella* and cotton leaf worm *Spodoptera littoralis*. These insects attack many important crops and in so doing cause great economic damage. The insecticidal-activity-enhanced compositions of the present invention show particular activity against health and nuisance insects such as flies, mosquitoes, roaches, crickets, silverfish, ants, earwigs, wasps, plant insects such as cicadas, moth larvae, beetles and their larvae, storage and material insects such as meal beetles, grain weevils, flat grain beetles, golden spider beetles, bread beetles, bean beetles, grain, flour and dry fruit moths, clothing moths, carpet beetles, Colorado beetles, fur beetles, and lard beetles, inter alia. Thus the admixtures are especially useful on cotton, corn, and soybean crops, soft fruit and top fruit such as apple, pear, peach, and citrus crops, inter alia. Other crops upon which the compositions and method of the invention may be employed include potatoes and other tuberous crops, and insecticides with which the capsicum is combined according to the present invention may include both contact and systemic insecticides, preferably contact insecticides such as parathion or other organic phosphate insecticide, DDT preferably together with copper sulfate, basic (Bordeaux mixture), Merck Index XI, number 2660, pages 414–415, or methoxychlor (Merck Index XI, number 5913, page 946), for example, for the control of insects such as aphids of various types.

As mentioned above, the compositions of the invention find particular application on cotton crops in which they give excellent control of the typical insects which attack cotton. Some of the most persistent insects which frequently cause considerable damage to this crop are insects of the order Noctuidae, otherwise known as noctuids. Such insects are difficult to control and observations suggest that camphechlor and other agents, which have been employed to control them, are of decreasing effectiveness owing to the development of insect resistance. As a group, noctuid insects include bollworm, pink bollworm, and cotton leaf worm, inter alia.

When employing a composition of the invention, the essential ingredients, viz., the capsaicinoid and the one or more active insecticidal agents are conveniently admixed together in a ratio of about 1:10 to 1:500, preferably 1:10 to 1:400 or 1:200 and especially 1:100 to 1:400 by weight. The percentage of capsaicinoid to total insecticide plus capsaicinoid by weight is generally between about 0.1 and 20 percent and preferably between about 0.2 and 10 percent by weight. One or more additional insecticides can be added into the composition provided only that they do not interfere with the synergistic interaction between the insecticide and the capsaicinoid. Concerning dose ranges: EPA-approved rates are the guidelines. For specific crops and insects, the EPA-labelled maximum doses, which are more effective with Capsyn™, may be significantly reduced and economic control of the pests still achieved. These lower doses are anticipated ultimately to be 50% or less, or even 10% or less, than the present EPA-registered application rates.

The composition of the invention can be employed in a wide variety of forms and can comprise a liquid or solid diluent optionally together with a surface active agent. It is most conveniently prepared in aqueous form immediately prior to use, for example, as a spray for insect-infested crops. One such method is commonly called "tank mixing" in which the two essential ingredients in their commercially-available forms are mixed together by the farmer or entomologist in the quantity of water most useful for the direct application. The concentration of the essential ingredients for application to a crop by conventional ground methods is preferably within the range of 0.001 to 10 percent, especially 0.005 to 5 percent by weight of the total composition, but more concentrated compositions containing up to 20 percent by weight may be desirable in the case of aerial sprays but with corresponding loss in economy. Concerning amounts of water: The amount of water used in conjunction with the insecticide and Capsyn™ can be adjusted upwardly or downwardly, as the particular application and available equipment require.

The compositions of the invention include not only those in suitable form for direct application but also concentrated primary compositions which can be supplied to the user for on-site dilution with a suitable quantity of water or other diluent before application. Such compositions may comprise a surface active agent in addition to the essential ingredients and typical examples are an aqueous solution, an aqueous dispersion or suspension, an aqueous emulsion, a concentrate emulsifiable in water, a dispersible powder, or a dusting powder. In such a concentrated primary composition or "concentrate", the concentration of essential ingredients to be "let down" by addition of water or other diluting fluid, including for some applications a finely-divided powder, can vary widely and can be for example from 5 to 95 percent by weight of the composition, as is well known in the art.

An emulsifiable concentrate, also known as a "miscible liquid", comprises a solution of the essential ingredients at least partially in a water-immiscible solvent in association with one or more emulsifying agents. An emulsion is then formed when the emulsifiable concentrate is let down by dilution with water.

A dispersible powder comprises the essential ingredients in finely-divided pulverulent form in association with one or more dispersing agents so that a stable aqueous dispersion of the essential ingredients is formed upon mixing the powder with water. A finely-divided inert solid diluent such as kaolin or celite is generally incorporated in the dispersible powder. A dusting powder comprises the essential ingredients intimately admixed with a solid pulverulent diluent, for example kaolin. Concerning dusts, etc.: Capsaicinoids can be incorporated into dusts and other non-aqueous systems by using the dry active capsaicinoids in anhydrous form, or in a suitable oil base.

As a further aspect, the invention includes a method of controlling insects which comprises applying a composition comprising the insecticide and the activity-enhancing capsaicinoid to the locus of the insects, that is, to the insects or their habitat, including the surrounding area. More particularly, the invention comprises a method for protecting plants, especially growing plants or crops, from insects by the use of such compositions applied most conveniently as a foliar spray at a rate, for example, of approximately 0.08 pounds to 5.5 pounds per acre, representatively about 0.09, 0.6, 1.0, and 1.2 pounds per acre, as illustrated by the Examples.

A wide variety of crops including cotton, maize, soybeans, soft fruit and top fruit can be protected by treatment with the insecticidally-enhanced composition of the invention, but the method of the invention finds particular application to cotton crops. Thus the invention includes a method for controlling insects on a cotton crop which comprises applying a composition of the invention to the cotton crop, in order to control, inter alia, noctuid insects such as bollworms, leaf worms and army worms. As previously stated, these insects are most satisfactorily controlled by application of the active ingredients, including the capsaicin, at a rate of approximately 0.22 to 5.36 pounds per acre and preferably about 0.45 to 2.25 pounds per acre. More than one application of a composite composition of the invention may frequently be desirable and, for example, treatment at intervals of 3 to 10 days is usually suitable.

DETAILED DESCRIPTION OF THE INVENTION

Description Of the Preferred Embodiments

The invention will be more fully understood by reference to the following Examples, which are given by way of illustration only and are not to be construed as limiting.

EXAMPLE 1

Control of bud worms, boll worms, and cabbage loopers

A. One gallon of Larvin and one gallon of Curacron 8E was mixed in eight gallons of water and sprayed at a rate of two gallons of liquid per acre. This solution was applied by air to a control plot. This amounts to 0.4 lb. of thiodicarb and 0.8 lb. of the active ingredient of Curacron, O-(4-bromo-2-chlorophenyl)-O-ethyl-S-propyl phosphorothioate (Profenfos), per acre.

B. A second 20 acre test plot was sprayed with the same insecticides at the same rate as above plus one gallon (8 lb.) of Capsyn™ per 60 acres (0.13 lb./acre). The Capsyn™ is equivalent to 0.0026 lb. capsaicinoids per acre.

After three days, there was no infestation remaining on the test plot. On the control plot, only 5% of the plants were free of worms.

To reaffirm the above findings, the control plot was resprayed with the mixture in B above at a rate of one gallon of Capsyn™ per 70 acres. In two days, all worms were on the ground and sick or dying.

The application of the mixture in B above was applied to 1250 acres of cotton and gave 98% control in every case. Even when 300 acres were treated with mixture B and showers were experienced two days later, the worms did not return.

EXAMPLE 2

Control of beet army worms on soybeans

The same insecticides at the same rate and Capsyn™ at the same rate as in Example 1-B were applied by air to beet army worms on soybeans. The result was that 98% of the plants were without worms following the spraying, in contrast to unsatisfactory control when the same insecticides at the same rate as in Example 1A were applied without Capsyn™.

EXAMPLE 3

Control of boll worms and beet army worms on cotton

A. Control plot was sprayed by air using one gallon Karate per 33 acres plus one gallon of methyl parathion per 16 acres. This amounts to 0.03 pound of methyl parathion and 0.06 pound of synthetic pyrethroids made to 2 gallons with water per acre.

B. The test plot was sprayed with the above mixture and one gallon of Capsyn™ per 35 acres, all combined with water so as to spray at a rate of 2 gallons per acre. This amounts to 0.0046 lb. capsaicinoids per acre.

The control plot had about 10% of the plants infested one day following application, whereas the test plot had less than 1% of the plants infested. This is considered excellent control on an economic basis.

EXAMPLE 4

Control of bud worms and boll worms in cotton and beans

A. One gallon of Lorsban plus 7 gallons of water were sprayed at the rate of two gallons per acre. This amounts to 1 lb. per acre of chlorpyrifos. It did not give a satisfactory kill, leaving an average of 24 worms per plant.

B. It was then reapplied after three days, but the spray then included Capsyn™. In this case, the test plot was sprayed with the mixture of A with 1/16 gallon of Capsyn™ instead of 1/16 gallon of water. This amounts to 0.23 lb. Capsyn™ per acre or 0.0026 lb. capsaicinoids per acre, in addition to 1 lb. chlorpyrifos per acre. After one day, there were no worms on the plants. All were dead or dying on the ground.

C. Unsatisfactory results similar to A were obtained with combinations of Lorsban and methyl parathion; Larvin plus Curacon plus methyl parathion; Lannate plus methyl parathion; and Lorsban plus methyl parathion plus Larvin, again applying the insecticide at labelled rates.

EXAMPLE 5

Control of bud worms and boll worms in cotton

An aqueous mixture of DuPont Lannate (methomyl), applied at a rate of 1 gallon (containing 2.4 lbs. of active ingredient per gallon) to a control plot of 4 acres, and methyl parathion, at 1 gallon to 35 acres, was applied by air to control worms in cotton. A test plot was sprayed with the same mixture plus 1 gallon Capsyn™ per 50 acres. This amounted to rates of 0.6 lb. methomyl, 0.015 lb. methyl parathion, and 0.0032 lb. capsaicinoids per acre, respectively.

The control without Capsyn™ was unsatisfactory. The control with Capsyn™ was excellent.

When the Capsyn™ solution was employed at a dose of 5–10 gallons per 1440 gallons of spray mixture and the mixture applied at a dosage of 2 gallons per acre, the treatment proved to be extremely effective. At the low dose of 0.5 gallons of Capsyn™, boll worm kill was increased from 50–60% without the capsaicin to 90%–100% with the capsaicin and, at the higher dose of 10 gallons of Capsyn™, the kill was approximately 100%.

EXAMPLE 6

Synergistic effect of Capsyn when used with pyrethrins on Japanese beetles

Actively feeding and mating Japanese beetles were sprayed with an aerosol of 10% Capsyn in water. The spray had no effect on their feeding or mating, the beetles appearing to be insensitive to it.

A 10% aqueous solution of Ortho Rose and Flower Insect Killer (pyrethrins) was applied to Japanese beetles as an aerosol. It interrupted feeding and mating, but did not cause mortality after three days. A 15% solution gave the same result.

An aqueous solution containing 10% of the Ortho Rose and Flower Insect Killer (pyrethrins) and 5% Capsyn was applied as an aerosol. Mortality was 80% after three days.

An aqueous solution containing 15% Ortho Rose and Flower Insect Killer (pyrethrins) and 3% Capsyn was applied to beetles as an aerosol. It inhibited feeding and mating, making the beetles unable to climb on vegetation. After three days they were all dead.

As already stated, marked insecticidal activity enhancement has been found to be provided by capsaicin, other capsaicinoids, and capsicum when employed in combination with normally-used insecticides. Particularly marked synergistic activity was found when employing a combination with pyrethrum and pyrethroids, and other normally-employed insecticides as further disclosed hereinafter and especially in the Examples, which permits considerable savings in these relatively-expensive materials as well as a shorter kill time and efficiency, and even kills where they were not substantially effected with the insecticidal agent alone. The activity-enhancing capsaicinoid ingredient of the present invention, when combined with pyrethrum or pyrethroids, or other normally-used insecticide, according to the present invention is usually employed in a weight ratio to the insecticide of about 1:10 to 1:500, preferably between about 1:10 to 1:200–400, and most preferably between about 1:100 to 1:400.

The activity-enhanced insecticidal compositions of the present invention are employed in normal or customary formulations, e.g., as solutions, emulsions, suspensions, or dispersions, powders, aerosols, foams, pastes, or granulates. The formulations are produced in known ways, e.g., by mixing the essential ingredients with extenders such as liquid solvents, especially water, and/or solid carrier materials. In addition surface-active agents, such as emulsifiers and/or dispersants and/or foam-generating agents, can be frequently be advantageously employed in the formulations. The use of auxiliary solvents is likewise frequently advantageous. Moreover, sticking agents, coloring agents and, in the case of some aerosols, propellant gases, can be included in the formulations. Combinations with other known insecticides and/or synergists, especially pyrethrum or synthetic pyrethroids, as well as mixtures with fungicides, growth regulators and plant nutrients are possible, so long as insecticidal effectiveness is not compromised. The content of the insecticidally-active ingredient or ingredients in such formulations can amount to as much as 80% to 99.9% by weight, preferably 90% to 99.8% by weight, not considering solvent or other diluents employed, with the remainder being the capsaicin activity-enhancing component according to the present invention, although higher percentages of capsicum to insecticide, e.g., up to 25% or even greater, may be employed, but are not generally acceptable from an economic standpoint.

As apparent from the foregoing, the performance parameters of the capsaicin-containing compositions of the present invention exceed the performance parameters of the known insecticidal agents when employed by themselves or in combination with another effective insecticidally-active ingredient by an unpredictable activity-enhancing amount, so that a synergistic combination is provided by the present invention, especially since capsaicin in the form of capsicum itself is found to be insecticidally inactive when employed alone.

FURTHER DISCLOSURE

Further Objectives of the Invention

Commercial cotton production in the United States involves not only the planting, culture and harvesting of the crop, but also a thorough knowledge of the many insect pests that feed on or damage the plant during the growing season prior to harvest. According to Insecticide and Acaricide Pests 15, Entomological Society of America (1990), among these damaging pests of the Class Insecta are:

Order Coleoptera, *Anthonomus grandis*, the boll weevil
Order Lepidoptera (Family Noctuidae)
*Pseudoletia unipuncta*, Armyworm
*Spodoptera eridania*, Southern armyworm
*S. exigua*, Beet armyworm
*Hellothis zea*, Bollworm (corn earworm)
*H. viresens*, Tobacco budworm
*Trichoplusia ni*, Cabbage looper
Order Homoptera, Aphids spp. (many species), Fleahoppers
Order Hemiptera, Tarnished plantbug; and
Order Thyranoptera, Thrips (many species).

Many different types of organic and inorganic insecticides have been developed, researched and used effectively in commercial programs against these and other insects when their presence and damage potential is apparent. Resistance to certain of these pesticides has developed within the insects which makes them ineffective and unreliable in control programs. Cancellation of the registration of others has made them unavailable for the growers. Currently 24 different insecticides are being used on cotton in the United States according to Crop Protection Chemicals Reference, C & P Press (1993).

Along with the development of these insecticides has come a thorough and detailed knowledge of the changing insect biologies. This understanding of the intricate relationship of insects and their environment and damage potential has developed into the science of Integrated Pest Management (IPM). The establishment of action thresholds, as well as scouting to determine damage potential and proper timing of application, assists in the selection of the best control technique to use. Follow-up evaluations determine the effectiveness of the action which was taken. All crops grown for food and fiber production have their own insect communities and require similar strategies.

FURTHER DISCUSSION OF THE CURRENT INVENTION

This invention or discovery first integrated the irritating properties of capsicum by using capsaicin-insecticidal combinations in an insect control program on cotton, to enable the capsicum to enhance and synergize the toxic effects of the selected insecticides. Prior evaluation of the insect population present in the study area determined that controls were necessary and that action should be taken. The primary insects present at the time were Beet armyworms and Cabbage loopers (Family Noctuidae).

The treatments used in the plots were:

Test Plot A (20 A. of cotton)

Larvin[1] 3.2 Flow. at 1 pt. (0.4 lb.ai**)/A. plus Curacron[2] 8E at 1 pt. (1.0 lb. ai)/A. plus Capsyn[3] at 1 gal./120 gal. (0.83% concentration)

*"a.i." means "active ingredient"
*"Flow. means "flowable liquid concentration"
[1]Larvin® Brand Thiodicarb, Rhone-Polenc Ag Company. E.P.A. Reg. No. 264-379
[2]Curacron® Brand Profenfos, CIBA-Geigy Corporation, E.P.A. Reg. No. 100-599
[3]Capsyn™—a solution of oleoresin capsicum in propylene glycol, essentially free of lipids, fats, carotenoids, and capsicum triglycerides (defatted oleoresin capsicum), and containing 2% capsaicinoids obtained from cayenne pepper pods, a product of Kalsec, Inc., Kalamazoo, Mich.

Test Plot B (Control-20 A. of cotton)

Larvin 3.2 Flow. at 1 pt. (0.4 lb. ai)/A. plus Curacron 8E at 1 pt. (1.0 lb. ai)/A.

The ingredients were tank-mixed in water at the ratio determined by the label and application rate. This solution was then transferred into the sprayer tank of the aircraft and applied at the rate of two gallons of spray per acre to the cotton foliage on the 20 A. plots. The Test Plot B was first and then the Capsyn™ was added to the same combination mixture and applied to Test Plot A.

An evaluation of the treated plots soon after indicated that the treatment on Test Plot B had provided only 5% control whereas the treatment with the same insecticidal mixture containing Capsyn™ on Test Plot A had provided 100% kill of the insect population on the foliage.

This study clearly exemplifies the synergistic effect of Capsyn™ when used with these insecticides which were chosen as examples of the many materials available to the cotton industry. The insecticides alone and/or in combination, without the Capsyn™, do not provide the immediate knockdown and control desired in insect control programs.

FURTHER CONTROL STUDIES

Other control studies show that the insecticidal activity of the insecticides Karate[4], Methyl parathion[5], Lorsban[6], Larvin[7], Curacron[8], and Lannate[9], when applied alone and/or in various combinations, against various insects on cotton or soy beans at registered rates, has been greatly enhanced by the synergistic affect of Capsyn™ when added to the spray mixtures.

[4]Karate® insecticide, ICI Americas, E.P.A. Reg. No. 10182-96

[5]Methyl parathion, PennCap M® insecticide, Elf Atochem North America, E.P.A. Reg. No. 4581-292

[6]Lorsban® insecticide, Dow Elanco, E.P.A. Reg. No. 62719-23

[7]Larvin®, op. cit.

[8]Curacron®, op. cit.

[9]Lannate®, E. I. DuPont de Nemours and Company, E.P.A. Reg. No. 352-370

FURTHER SUMMARY OF FINDINGS AND USES

Although the synergistic activity of the Capsyn™ insecticide combinations (ICS) control programs has been shown, further studies will refine and optimize the schedules required in a particular case for control as directed by the insecticide label. By assuring the Pest Management Specialist that better and quicker control is possible with Capsyn™-ICS in the tank-mixture, that lower rates of the toxicant may be possible, or that the spray schedule can be opened up and thus not applied as often, the result will be a reduced insecticide usage in the crop production. This reduction of insecticide use should extend the life of currently-used materials by delaying the development of resistance in the insect populations.

Various Capsyn™-ICS studies to date have been with material applied by aircraft in little water diluent in relation to the toxicant. No incompatibilities have been seen in the concentrated combinations. Thus there should be no problems with more dilute control programs or in ground applications where more water is generally required for distribution of the spray materials. Further studies will determine the optimum concentrations of Capsyn™ required in the various spray mixtures to obtain the same synergistic effects on various insects.

The versatility and safety of the synergistic insecticidal capabilities of Capsyn™ is also of value in other control programs on many other crops such as potatoes, sweet corn, and other field and vegetable crops. Capsyn™-ICS also have a place in controlling insect pests on ornamentals in the landscape and nursery industries. Capsyn™-ICS can also be used in aerosol sprays for household insect control. Synergized formulations of insecticides are well established for this use.

One main factor in the use of Capsyn™ in a spray program is its innate warning to the user of its presence. The resulting sprays containing Capsyn™ are extremely noxious and incite coughing in human beings, thereby making the combinations safer for use than when the capsicum is not present. This safety factor results because protective breathing precautions cannot be forgotten when using the compositions of the present invention, whereas there is often a tendency to neglect protection when normal commercial insecticides are employed alone.

The use of insecticide combinations containing Capsyn™ will be a very important part of Integrated Pest Management (IPM) programs against innumerable economic and regulatory insect species.

It is therefore seen that an improved and highly-advantageous insecticidal composition, suitable for all of its intended purposes and uses, and having a high order of activity enhancement in contrast with the same insecticidal composition not including the activity-enhancing amount of capsaicin, other capsaicinoids, or capsicum containing the same, as required according to the present invention, is provided by the present invention, with all of its attendant advantages and use.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

We claim:

1. An insecticidal composition comprising as essential ingredients an effective insecticidal amount of (A) an organophosphorus insecticidal ingredient, plus (B) an activity-enhancing amount of a capsaicinoid, the weight ratio of (B) to (A) being between about 1:10 and 1:500.

2. A composition according to claim 1, wherein the weight ratio of (B) to (A) is between about 1:10 and 1:200–400.

3. A composition according to claim 1, wherein the weight ratio of (B) to (A) is approximately 1:100 to 1:400.

4. A composition of claim 1 wherein the insecticidal activity enhancer is capsaicin.

5. A composition of claim 4, wherein the insecticide is selected from the group consisting of chlorpyrifos, phosphorothioates, parathions, and profenfos.

6. A composition of claim 1 wherein the capsaicinoid is in the form of an essentially lipid-free and optionally aqueous solution thereof in a polyol.

7. An insecticidal composition comprising a mixture of (A) an organophosphorus insecticidal ingredient or ingredients, and (B) an activity-enhancing amount of capsaicin in a ratio between about 1:10 to 1:500 by weight, the concentration of the insecticidal ingredient or ingredients being an insecticidally-effective concentration.

8. A composition of claim 7 in the form of a dilutable concentrate.

9. A concentrate of claim 8 wherein the composition is dilutable with water.

10. A composition of claim 7, wherein the insecticidal activity enhancer is capsaicin and the insecticide is a parathion insecticide.

11. A method of killing insects comprising the step of spraying a combination of (A) an effective insecticidal amount of an organophosphorus insecticidal ingredient, plus (B) an activity-enhancing amount of a capsaicinoid, upon the insect or upon its habitat, the weight ratio of (B) to (A) being between about 1:10 and 1:500.

12. A method of claim 11 wherein the capsaicinoid is in the form of an essentially lipid-free and optionally aqueous solution thereof in a polyol.

13. A method for controlling insects comprising contacting insects or their habitat with an insecticidally-active composition of claim 1.

14. A method of claim 13, wherein the insecticidal activity enhancer is capsaicin and the insecticide is a parathion insecticide.

15. A method for controlling insects comprising contacting insects or their habitat with an insecticidally-active composition of claim 2.

16. A method for controlling insects comprising contacting insects or their habitat with an insecticidally-active composition of claim 3.

17. A method of controlling insects which comprises applying, to the insects or their habitat, an insecticidally-effective amount of a composition of claim 7.

18. A method of claim 17, wherein the concentration of active ingredients in the composition is between about 0.001 and 20% by weight.

19. A method of claim 17, wherein the concentration of active ingredients in the composition is between about 0.005 and 10% by weight.

20. A method of claim 17, wherein the habitat is living plants.

21. A method of claim 20, wherein the plants are cotton, soybeans corn, garden vegetables, fruits, or flowers.

22. A method of claim 20, wherein the plants are cotton plants.

23. The method of claim 20, wherein the composition is applied by spraying.

24. The method of claim 23, wherein the composition is applied by aerial spraying.

25. A method of claim 17, wherein the weight ratio is between about 1:100 and 1:400 by weight.

26. A method according to claim 17 in which active ingredients are applied at a rate of about 0.8 to about 5.5 pounds per acre.

27. A method of claim 17, wherein the composition is applied at a rate of about 2.2 to about 5.36 pounds per acre.

28. A method of claim 17, wherein the composition is applied at a rate of about 0.45 to about 2.25 pounds per acre.

29. A method of claim 17, wherein the insect controlled is selected from boll worms, army worms, bud worms, loopers, and beetles.

30. A method of claim 17, wherein the insecticidal activity enhancer is oleoresin capsicum.

31. A method of claim 17, wherein the insecticidal ingredient is selected from the group consisting of chlorpyrifos, phosphorothioates, parathions, and profenfos.

32. A method of claim 31, wherein the insect controlled is selected from the group consisting of bud worms, boll worms, cabbage loopers, army worms, and beetles, and the habitat protected is a plant selected from the group consisting of cotton, beans, corn, garden vegetables, fruits and flowers.

33. A method of enhancing the insecticidal activity of an organophosphorus insecticide composition comprising the step of including in said composition an effective insecticidal-activity-enhancing amount of a capsaicinoid, the weight ratio of capsaicinoid to insecticide being between about 0.1 and about 20% by weight.

34. A method of claim 33 wherein the weight ratio of capsaicinoid to insecticide is between about 0.2 and about 10% by weight.

35. A method of claim 33 wherein the insecticidal activity enhancer is capsaicin.

36. A method of claim 35, wherein the enhancement relates to the protection of a plant selected from the group consisting of cotton, beans, corn, garden vegetables, fruits, and flowers against an insect selected from the group consisting of bud worms, boll worms, cabbage loopers, army worms, and beetles.

37. A method of claim 36 wherein the enhancement is of an insecticide selected from the group consisting of chlorpyrifos, phosphorothioates, parathions, and profenfos.

38. A method of claim 37 wherein the capsaicin is in the form of an essentially lipid-free and optionally aqueous solution thereof in a polyol.

39. A method of claim 35 wherein the insecticidal activity enhancer is capsaicin and the insecticide is a parathion insecticide.

40. A method of claim 34 wherein the insecticidal activity enhancer is capsaicin.

41. A method of claim 33, wherein the insecticide is selected from the group consisting of chlorpyrifos, phosphorothioates, parathions, and profenfos.

42. A method of claim 33 wherein the capsaicinoid is in the form of an essentially lipid-free and optionally aqueous solution thereof in a polyol.

* * * * *

UNITED STATES PATENT AND TRADEMARK OFFICE
CERTIFICATE OF CORRECTION

PATENT NO. : 5,525,597
DATED : July 1, 1996
INVENTOR(S) : Gary C. Hainrihar

It is certified that error appears in the above-indentified patent and that said Letters Patent is hereby corrected as shown below:

Column 1, line 29: "specially" should read
    -- especially --.

Column 6, line 7: "Parthion" should read
    -- Parathion --.

Column 7, line 60: "Hellothis" should read
    -- Heliothis --.

Column 13, lines 10: "Hellothis" should read
    -- Heliothis --.

Signed and Sealed this

Fifteenth Day of October, 1996

*Attest:*

BRUCE LEHMAN

*Attesting Officer*     *Commissioner of Patents and Trademarks*